United States Patent
Selcho et al.

(10) Patent No.: US 10,165,937 B2
(45) Date of Patent: Jan. 1, 2019

(54) CONFIGURABLE ANESTHESIA SAFETY SYSTEM

(71) Applicant: Karl Storz Imaging, Inc., Goleta, CA (US)

(72) Inventors: Michael Selcho, Salt Lake City, UT (US); Hans-Uwe Hilzinger, Tuttlingen (DE); Devon Bream, Manhattan Beach, CA (US)

(73) Assignee: Karl Storz Imaging, Inc., Goleta, CA (US)

( * ) Notice: Subject to any disclaimer, the term of this patent is extended or adjusted under 35 U.S.C. 154(b) by 109 days.

(21) Appl. No.: 13/675,825

(22) Filed: Nov. 13, 2012

(65) Prior Publication Data

US 2014/0135582 A1 May 15, 2014

(51) Int. Cl.
*A61B 1/267* (2006.01)
*A61B 1/00* (2006.01)

(52) U.S. Cl.
CPC ........... *A61B 1/267* (2013.01); *A61B 1/0005* (2013.01)

(58) Field of Classification Search
CPC ... A61B 1/267; A61B 1/0005; A61B 1/00045; A61B 1/04; A61B 1/00112; A61B 1/00039; A61B 17/00; A61B 2017/00017–2017/0023; G06F 3/04817; G06F 3/147; G06F 3/167
USPC ........................................................ 600/188
See application file for complete search history.

(56) References Cited

U.S. PATENT DOCUMENTS

| | | |
|---|---|---|
| 5,788,688 A | 8/1998 | Bauer et al. |
| 5,827,178 A | 10/1998 | Berall |
| 6,543,447 B2 | 4/2003 | Pacey |
| 6,655,377 B2 | 12/2003 | Pacey |
| 6,890,298 B2 | 5/2005 | Berci et al. |
| 7,044,909 B2 | 5/2006 | Berci et al. |
| 8,029,440 B2 | 10/2011 | Birnkrant et al. |
| 8,069,420 B2 | 11/2011 | Plummer |
| 8,627,219 B2 | 1/2014 | Wang et al. |
| 9,119,700 B2 | 9/2015 | Boukhny |
| 9,283,347 B2 | 3/2016 | Heesch |
| 2003/0171740 A1* | 9/2003 | Stiller et al. ................ 606/1 |
| 2004/0024384 A1* | 2/2004 | Novak .......................... 606/1 |
| 2006/0152516 A1* | 7/2006 | Plummer ..................... 345/538 |
| 2008/0249370 A1* | 10/2008 | Birnkrant et al. ........... 600/188 |
| 2011/0088694 A1* | 4/2011 | Tobia et al. ............ 128/204.23 |
| 2012/0278759 A1* | 11/2012 | Curl et al. ................... 715/804 |
| 2014/0135648 A1 | 5/2014 | Holoien et al. |

(Continued)

OTHER PUBLICATIONS

OR 1 (R) Essential Drawings Drawn by: SS Dated: Sep. 9, 2008 13 pages.

(Continued)

*Primary Examiner* — Jacqueline Johanas
*Assistant Examiner* — Tessa Matthews
(74) *Attorney, Agent, or Firm* — Whitmyer IP Group LLC

(57) ABSTRACT

A medical image routing system that allows for a user to override the current routing of medical image data such that a user need only activate an input device and the first medical image data routing to a display(s) is automatically interrupted and second medical image data is automatically routed to the display(s). Upon activation of the input device a second time, the first medical image data routing is automatically reestablished and the second medical image data is automatically interrupted.

5 Claims, 7 Drawing Sheets

(56) References Cited

U.S. PATENT DOCUMENTS

2016/0000299 A1  1/2016  Itai
2016/0037998 A1  2/2016  Kawashima et al.

OTHER PUBLICATIONS

OR1(R) Essential—Instruction Manual; (c) 2009 Karl Storz Endoscopy-America, Inc.; 36 pages.
U.S. Office Action U.S. Appl. No. 14/932,621 dated Jan. 11, 2017 27 Pages.
U.S. Office Action U.S. Appl. No. 14/932,621 dated Mar. 25, 2016 24 Pages.

* cited by examiner

CONFIGURABLE ANESTHESIA SAFETY SYSTEM

FIELD OF THE INVENTION

The system relates to an image routing system, and more particularly to a medical image routing system utilized in an operating room providing streamlined image routing in the event of an emergency.

BACKGROUND OF THE INVENTION

A wide variety of operating room systems are known for performing both diagnostic and surgical procedures. In particular, systems have been provided that allow a surgeon to perform a procedure with a variety of medical and operating room equipment. This equipment ranges from visual imaging tools (e.g., endoscopes, cameras, etc.) and systems, to medical devices (e.g. tools for cutting, grasping, extracting, irrigating, etc.), and other operating room equipment.

In particular, operating room visualization equipment has been provided that allows for visualization of the interior of an organ or joint while a surgeon is conducting a procedure. These visualization systems allow for a surgeon to view, typically on a surgical monitor placed either in or adjacent to, the sterile environment, a location inside the body where the procedure is being performed. These systems have further allowed for the recording of still pictures and video recordings of the area and procedure. Not only have the surgeon and those in the operating room been able to view the surgical site on the surgical monitor, but systems have further provided for the transfer of visualization information via a network connection to remote locations from the operating room. In this manner, individuals have had the capacity to view a surgical procedure from different locations. This has proved to be a very helpful educational tool (e.g. medical students can view a medical procedure from a class room) and has allowed for specialists to view the surgical procedure from a distance to provide expert analysis and input to the surgeon.

A number of medical procedures require the patient be maintained under anesthesia, typically by means of IV administered anesthesia or a gas mixture administered to the patient, or both. In this case, ventilation is provided to the patient, which may be provided through an endotracheal tube inserted into the trachea. It should be noted that when the tube is inserted, the patient is asleep hyperoxygenated and then paralyzed for the procedure, and therefore not breathing. As the ventilator is not yet in operation, the physician must work quickly to insert the endotracheal tube.

The insertion of this tube involves risks that the anesthesiologist seeks to avoid or at least minimize. It is estimated that between one in 6,000 to one in 8,000 general anesthesia procedures result in death. There are of course many causes but of these it is estimated that about one third of them are caused by the intubation procedure.

Some obstacles encountered by the anesthesiologist include; the remoteness of the location where the tube is to be positioned, the consequent restriction of view as the tube is inserted, variations and anomalies in the anatomy of the patients, an uncomfortable and unnatural position for the anesthesiologist while holding the instrument, the potential need to change blades during the procedure, and the necessity for rapid intubation.

With the advent of endoscopic equipment and small cameras, instrumentation can enable viewing of the cords and larynx on a video screen facilitating the intubation of the patient in a relatively quick and safe manner. A number of video laryngoscopes have been known including U.S. Pat. Nos. 6,655,377; 6,543,447; 6,890,298; 7,044,909 and 8,029,440. Typically, these video laryngoscopes route video feeds to dedicated video monitors located adjacent to the laryngoscope (e.g. a video screen mounted beside or right on the handle of the laryngoscope).

As operating room control systems develop, the use of video displays and control systems continues to expand. For example, U.S. Pat. No. 8,069,420 to Roderick Plummer (the Plummer patent) discloses an operating room system that allows for videos to be displayed on screens in the operating room.

However, while great steps have been made in the presentation of endoscope video imaging in an operating room system, the integration of video laryngoscopes into the operating room control system has not been effectively addressed. In current systems, the intubation process occurs with a system separate and apart from the operating room system. However, if during a surgical procedure it becomes necessary to re-intubate the patient, time is critical. Having to move the operating room equipment aside, moving the laryngoscope equipment in, intubating the patient, moving the laryngoscope equipment aside and moving the operating room equipment back into place can mean delayed time to intubate the patient and increased time under anesthesia, both of which are highly undesirable.

SUMMARY OF THE INVENTION

Accordingly, it is an object of the present invention to provide an operating room system that integrates both a video laryngoscope and a video endoscope into a single centralized operating room system.

It is another object of the present invention to provide an operating room system that allows an anesthesiologist to quickly and efficiently intubate a patient by use of a video laryngoscope providing a video feed to an operating room system monitor.

It is still another object of the present invention to provide an operating room system that allows an anesthesiologist to quickly and efficiently interrupt a video feed to an operating room system monitor such that the operating room system monitor temporarily displays a video laryngoscope video feed to aid an anesthesiologist to re-intubate a patient.

These and other embodiments of the present invention are achieved by the provision of an operating room control system that includes a computer, an interface that includes input connections for an imaging device generating endoscope image data, at least one display for displaying the endoscope image data, an input device and a video laryngoscope, where the video laryngoscope generates laryngoscope image data. The system is provided such that upon activation of the input device, the routing of endoscope image data to the display is interrupted and laryngoscope image data is instead shown on the display. The system is further provided such that upon activation of the input device a second time, the routing of laryngoscope image data to the display is interrupted and endoscope image data is instead shown on the display.

It is contemplated that a video laryngoscope may be integrated into a centralized operating room control system such that the video laryngoscope may utilize the same display(s) utilized by a surgeon during a medical procedure. Thus no separate laryngoscope display and associated equipment need be positioned in the operating room. Rather, the anesthesiologist can use the surgical display already located in the operating room. However, the challenge is how to quickly and easily switch between multiple different imaging sources (endoscope and laryngoscope).

Under normal surgical conditions, this would not normally be a problem because the patient is intubated prior to any surgical procedure occurring. The anesthesiologist has the time to insert the endotracheal tube into the patient's trachea while viewing the patient's throat/airway on the surgical monitor. Once the endotracheal tube is put in place, the laryngoscope is removed and the endotracheal tube is connected to a ventilator. At this point, the anesthesiologist will monitor the patient's vital signs and the administration of anesthesia. The surgeon may then use the various displays to perform the surgical procedure as needed.

However, in the event that it is determined that a patient needs to be re-intubated, it is critical that the intubation process happen quickly as the patient is not breathing. The challenge occurs if the display used by the anesthesiologist for intubation is currently being used by the surgeon. This becomes even more challenging for systems that allow for complex routing of video information, for example, saving of the endoscope image data to one or more storage devices.

Accordingly, an input device is provided that allows the anesthesiologist at a single location to override the routing of the endoscope image data to the surgical monitor and automatically route the laryngoscope image data to the surgical monitor. This allows the anesthesiologist to immediately take control of the display to re-intubate the patient and re-connect the endotracheal tube to the ventilator. It is further understood that from the same location the anesthesiologist can reconstitute the routing of the endoscope image to the surgical display, as well as to the configured storage devices by activation of the input device. This effectively allows the anesthesiologist to instantly commandeer the display system for intubation purposes and then turn the display system back over to the surgeon without the need for any reprogramming, thereby reducing the time the patient is under anesthesia and minimizing any potential intubation time.

The input device may comprise any type of device that allows for interruption of the endoscope image data and automatic connection of the laryngoscope image data and vice versa when the anesthesiologist has finished the intubation process.

In one embodiment, the input device may comprise an icon located on a touchscreen accessible by the anesthesiologist. However, it should be noted that virtually any type of input device could be used including, for example, an emergency intubation button may be positioned in the vicinity of the anesthesiologist. It is further contemplated that upon activation of the input device, the laryngoscope image data may automatically be displayed on the main surgical monitor, on a secondary surgical monitor, on the touchscreen provided for the anesthesiologist or any combination thereof.

In the touchscreen embodiment, it is contemplated that additional medical information may be displayed on the touchscreen for the anesthesiologist including, for example, patient vital signs, anesthesia levels being administered, settings of the ventilation, and the like. The system will be programmed so that the laryngoscope image data is presented on the display desired. In the event the anesthesiologist desires the laryngoscope image data be displayed on the touchscreen, it is contemplated that the laryngoscope image data can immediately be displayed in a screen over top of the medical data being displayed on the touchscreen to provide a large image for the anesthesiologist. It should be understood that this is only a few embodiments and arrangements for the emergency display of laryngoscope image data and those of skill in the art may come up with many ways of automatically routing the laryngoscope image data without deviating from the invention.

For this application the following terms and definitions shall apply:

The term "network" as used herein includes both networks and internetworks of all kinds, including the Internet, and is not limited to any particular network or inter-network.

The terms "coupled", "coupled to", "coupled with", "connected", "connected to", and "connected with" as used herein each mean a relationship between or among two or more devices, apparatus, files, programs, media, components, networks, systems, subsystems, and/or means, constituting any one or more of (a) a connection, whether direct or through one or more other devices, apparatus, files, programs, media, components, networks, systems, subsystems, or means, (b) a communications relationship, whether direct or through one or more other devices, apparatus, files, programs, media, components, networks, systems, subsystems, or means, and/or (c) a functional relationship in which the operation of any one or more devices, apparatus, files, programs, media, components, networks, systems, subsystems, or means depends, in whole or in part, on the operation of any one or more others thereof.

In one embodiment of the present invention an operating room control system is provided comprising a computer having a network connection, and a storage accessible by the computer. The system also includes an interface coupled to the computer that provides for connection to an imaging device generating endoscope image data, an input device, and a video laryngoscope, where the video laryngoscope generates laryngoscope image data. The system further includes a display coupled to the interface and endoscope image data is routed to and shown on the display when an imaging device is connected to the system. The system is provided such that upon activation of the input device, routing of the endoscope image data to the display is interrupted and laryngoscope image data is routed to the display when a video laryngoscope is connected to the system.

In another embodiment of the present invention an operating room control system is provided comprising a computer having a network connection, a storage device accessible by the computer, and an interface coupled to the computer. The system also includes an imaging device coupled to the interface and generating endoscope image data and an input device coupled to the interface. The system further includes a video laryngoscope coupled to the interface and generating laryngoscope image data, and a display coupled to the interface and endoscope image data is routed to and shown on the display. The system is provided such that upon activation of the input device, routing of the endoscope image data to the display is interrupted and laryngoscope image data is automatically routed to the display. The system is further provided such that upon activation of the input device a second time, routing of the laryngoscope image data to said display is interrupted and routing of endoscope image data is automatically routed to the display.

Other objects of the invention and its particular features and advantages will become more apparent from consideration of the following drawings and accompanying detailed description.

DETAILED DESCRIPTION OF THE INVENTION

Figure 1:
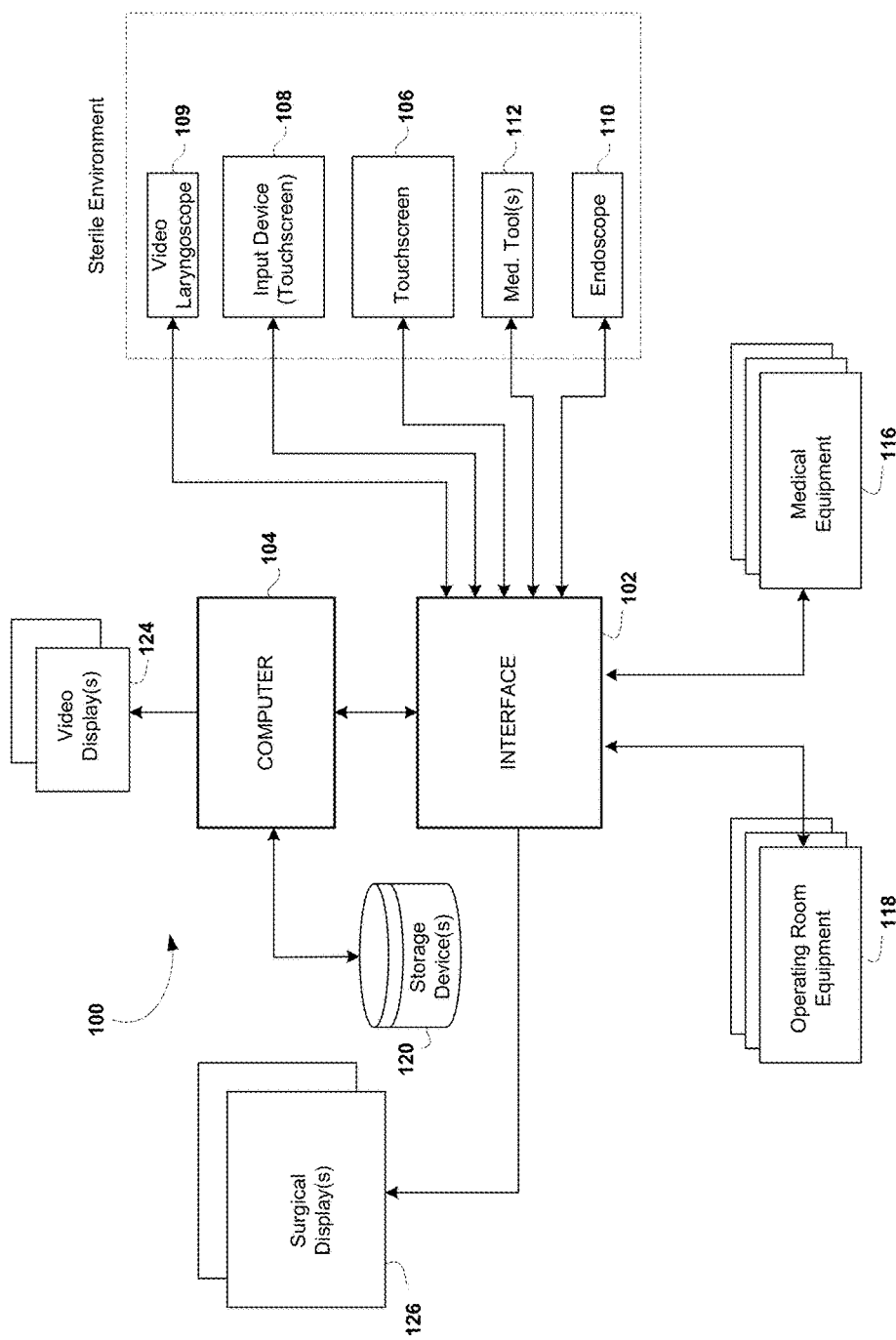
FIG. 1 is a block diagram of an advantageous embodiment of the present invention.

Referring now to the drawings, wherein like reference numerals designate corresponding structure throughout the views.

FIG. 1 is a block diagram of operating room control system 100 that generally includes an interface 102 connected to a computer 104. The interface 102 would typically be positioned or located in the operating room in proximity to the various equipment connected thereto and in one embodiment, would be rack-mounted. It is further understood that computer 104 may also be located in the operating room and rack-mounted, however, this is not required as the interface 102 could be coupled to computer 104 via a network connection.

Connected to interface 102 is touchscreen 106, which provides an interface for a user to control and to interface with operating room control system 100. Touchscreen 106 is shown positioned in the sterile environment and is accessible by a surgeon performing a procedure. The touchscreen 106 may comprise virtually any type of commercially available touchscreen device and would typically be mounted on a boom or arm allowing the user to position the touchscreen 106 in a manner convenient for use (e.g., adjacent to or over the patient).

An input device 108 (touchscreen) is also illustrated positioned in or adjacent to the sterile environment and connected to interface 102. Input device 108 may be provided for an anesthesiologist to view the patient's vital signs and control the administration of anesthesia to the patient. It is understood that input device 108 may provide control of various medical equipment 116, and may have the ability to access, for example, the hospital information system to pull up the patient's records and information. Still further, the anesthesiologist may be provided with the ability to record or save the information presented on input device 108 as desired in a manner and to any of the storage devices previously discussed. The idea is to provide maximum flexibility to the system users to increase safety, efficiency and ease of use.

Also shown in FIG. 1 is video laryngoscope 109, which may comprise any commercially available laryngoscope that is capable of generating digital image data. As previously discussed, it is common to intubate a patient prior to a surgical procedure in order to place an endotracheal tube in the patient's trachea, which is in turn connected to a ventilator to provide oxygen and other medical/anesthetic gases to the patient during the surgical procedure. The video laryngoscope 109 generates laryngoscope image data, which is transmitted to the operating room system to be shown on the surgical display and/or the video monitor as desired. The laryngoscope image data provides the anesthesiologist a view of the inside of the patient's throat and trachea to aid the anesthesiologist in the intubation procedure. Once endotracheal tube it properly inserted, the video laryngoscope 109 is withdraw and the surgeon can utilize the surgical display(s) 126 and video display(s) 124 to display endoscope image data during the surgical procedure. During the surgical procedure, endoscope image data is going to be routed to the display(s) based on the surgeon's preferences and is also being routed to selected storage devices according to the surgeon's preferences. The input device 109 allows the anesthesiologist to quickly and efficiently route laryngoscope image data to a display(s) in the event that an emergency intubation procedure is required.

Accordingly, the input device 109 allows the anesthesiologist at a single location to override the routing of the endoscope image data and automatically route the laryngoscope image data to surgical display(s) 126 and/or video display(s) 124. It is further understood that input device 109 also allows the anesthesiologist to reestablish the routing of the endoscope image to surgical display(s) 126 and/or video display(s) 124, as well as to the configured storage devices. This effectively allows the anesthesiologist to instantly take control of the various displays for emergency intubation purposes and then turn the display system back over to the surgeon without the need for any reprogramming thereby reducing the time the patient is under anesthesia and minimizing any potential intubation time.

The input device 109 may comprise any type of device that allows for interruption of the endoscope image data and automatic connection of the laryngoscope image data and vice versa when the anesthesiologist has finished the intubation process and, as illustrated in FIG. 1, may be associated with a touchscreen. For example, in one embodiment, the input device 109 may comprise an icon located on a touchscreen accessible by the anesthesiologist.

It is further contemplated that upon activation of the input device, the laryngoscope image data may automatically be displayed on the main surgical display(s), on a secondary display(s) (e.g., video display 124), on the touchscreen provided for the anesthesiologist or any combination thereof. The idea is to provide maximum flexibility for the anesthesiologist to be able to easily view the laryngoscope image data to intubate the patient and then quickly turn the display(s) back over to the surgeon for minimum interruption of the surgical procedure.

While an icon positioned on a touchscreen is envisioned as one embodiment of input device 109, virtually any type of input device could be used including, for example, an emergency intubation button placed in the vicinity of the anesthesiologist that will automatically route laryngoscope image data as previously discussed.

Also illustrated in FIG. 1 is endoscope 110 and medical tool(s) 112 connected to interface 102. Endoscope 110 may comprise virtually any type of video endoscope that allows for visualization of a surgical site inside of the body and may be flexible or rigid and have a detachable or integral camera. It is further contemplated that endoscope 110 may utilize a wired or wireless connection to interface 102 and have a CCD or CMOS imager (not shown) positioned on the endoscope for converting received light to a digital image stream.

Likewise, medical tool(s) 112 may comprise a wide variety of medical tools used by the surgeon including, but not limited to: catheterization devices, bi-polar cutting devices, lasers, rotating cutting devices, cell collection devices, suction devices and the like. It is understood that many of these medical tools 112 may be manufactured by different companies and therefore the command and control signals for each of the medical tools may differ. Interface 102 is provided to interface between the numerous differing types of signal formats such that the user may control a medical tool(s) from the touchscreen 106 if desired.

Medical equipment 116 is illustrated having a number of boxes to indicate that there may be a plurality of medical equipment 116 connected to interface 102. Typically medical equipment 116 will be rack-mounted on a rack with wheels allowing for the equipment to be placed conveniently and in proximity to the sterile environment. Medical equipment 116 will vary depending on the procedure being performed, however, to provide some context to the types of equipment that medical equipment 116 may comprise, a non-exhaustive list is provided including: insufflation equipment, irrigation equipment, vacuum equipment and the like. It should be understood that a great number of different types of equipment may be used depending upon the procedure to be performed. As with medical tool(s) 112, it is contemplated that medical equipment 116 will be equipment manufactured by many different companies and therefore have command and control signals with diverse formats and requirements. Accordingly, interface 102 is provided to send and receive data to and from medical equipment 116 such that the medical equipment 116 may be controlled from touchscreen 106.

Also shown in FIG. 1 is operating room equipment 118 connected to interface 102. Like medical equipment 116, operating room equipment 118 is controllable from either touchscreen 106 or touchscreen 114. Operating room equipment 118 may comprise a wide variety of equipment that may be desirable to control by the surgeon or nurse including, but not limited to, the operating room lights, the operating room blinds or shades, and the positioning of the operating room table.

Still further, storage device(s) 120 is shown connected to computer 104. Storage device(s) 120 may comprise virtually any type of digital storage device including, solid state hard drive devices, magnetic hard drives devices, optical drive devices, removable storage devices and the like. For example, it may be desired to record a part or all of the procedure from the video endoscope 110 to a DVD inserted into computer 104. However, it may further be desire to save a part or all of the procedure to a hard drive device in the hospital information system for the hospitals records. Still further, the surgeon may desire to save a part or all of the procedure directly to a storage device on the surgeon's computer in the surgeon's office.

Video display(s) 124 is illustrated connected to computer 104. It should be understood that operating room control system 100 allows for video feeds to remote locations for telesurgery and teleconferencing such that a surgeon at a remote location could view the surgical procedure and provide input or comments to the surgeon performing the procedure. In addition, a video feed could be provided to a classroom environment for educational purposes so that medical students have the opportunity to see a particular medical procedure from a remote location.

Surgical display(s) 126 is shown connected to interface 102 and may comprise one or more surgical monitors positioned in the operating room. Typically a main surgical monitor (typically a large (40"-60") flat panel display) is provided in the operating room and quite often, numerous surgical monitors are positioned at various locations in the operating room. It is contemplated that the video feed from the video endoscope 110 will be displayed on surgical display(s) 126. While surgical display(s) 126 are shown connected to interface 102, it is understood that they may alternatively, be directly connected to computer 104.

Figure 2:
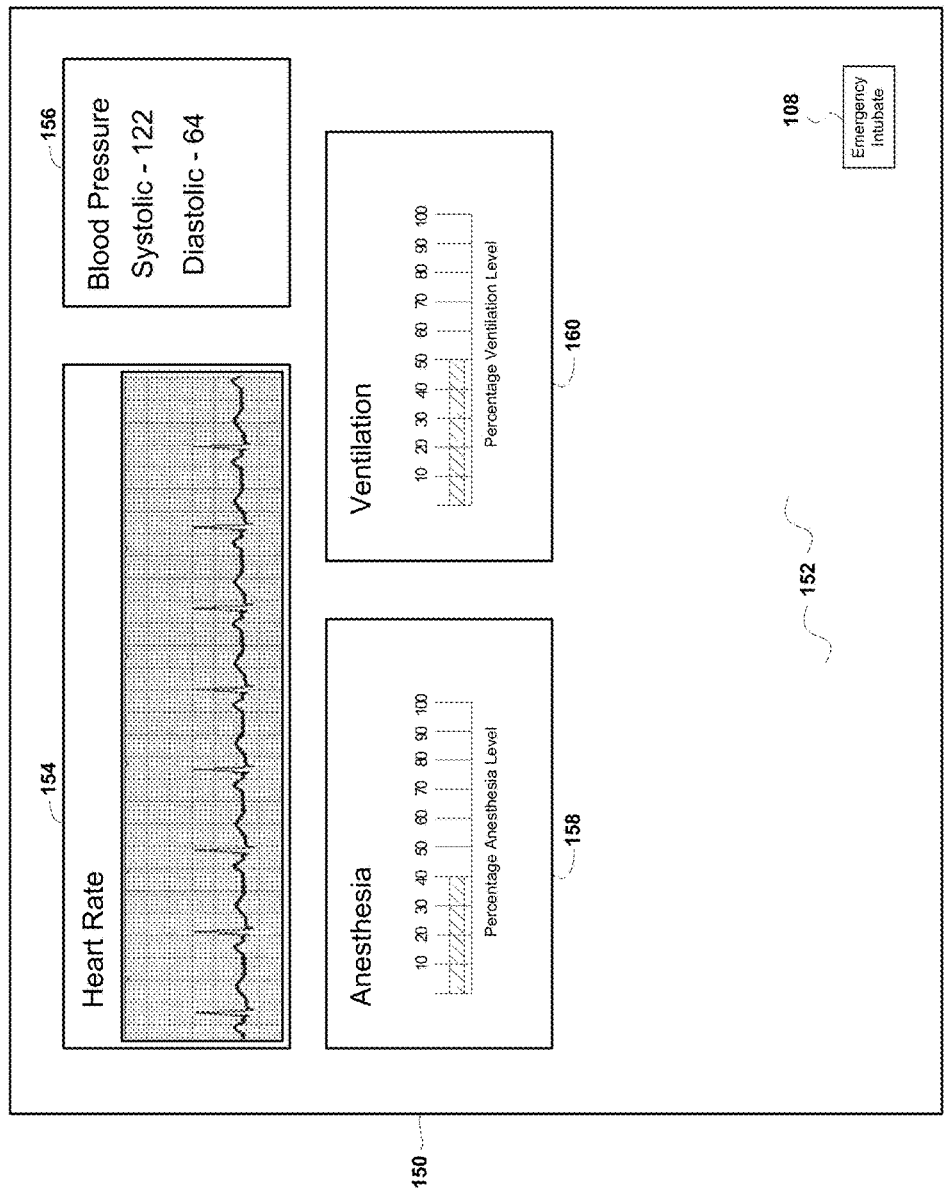
FIG. 2 is an illustration of an embodiment of the present invention according to FIG. 1.

Turning now to FIG. 2, an illustration of one embodiment of the present invention is provided in which various interfaces are provided on the front panel 152 of a touchscreen 150 having the input device 108 positioned thereon in the form of an icon.

The layout and type of medical information presented on the touchscreen 150 is merely presented to be typical of some information that may advantageously be presented to the anesthesiologist and is not intended to comprise a comprehensive list. It will be understood by those of skill in the art that numerous and varied medical information may be presented on the touchscreen depending upon the type of medical procedure being performed. In this particular example, a heart rate interface 154, a blood pressure interface 156, an anesthesia interface 158 and a ventilation interface 160 are all presented.

In the event that the anesthesiologist determines that the patient needs to be intubated (or re-intubated), the anesthesiologist need only touch the input device (emergency intubate icon) 108 located on the touchscreen 150.

Figure 3:
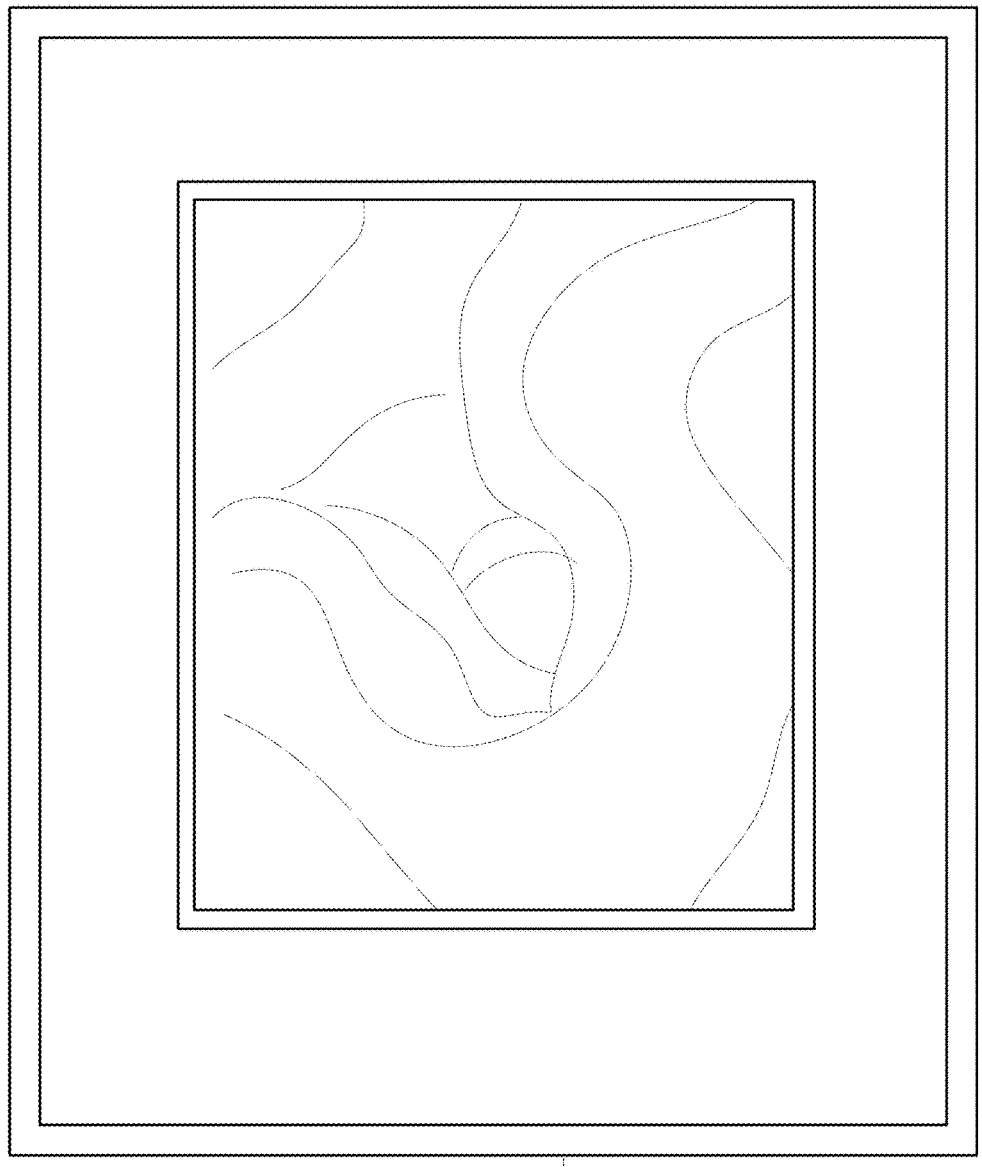
FIG. 3 is an illustration of a monitor according to an embodiment of the present invention of FIG. 1.
Figure 4:
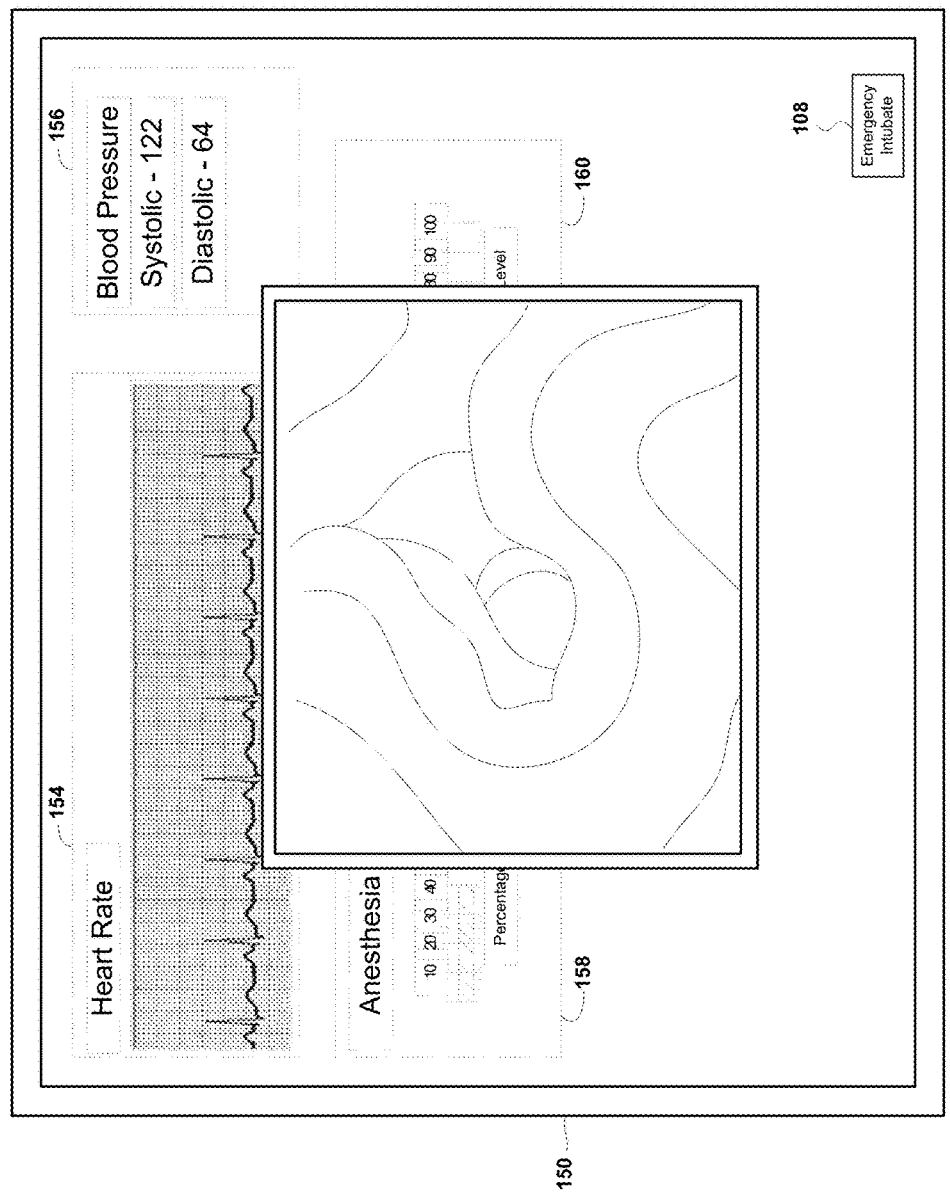
FIG. 4 is an illustration of a monitor according to an embodiment of the present invention of FIG. 2.

FIGS. 3 and 4 illustrate several embodiments of how the laryngoscope image data may be presented to the anesthesiologist. For example, FIG. 3 shows the laryngoscope image data automatically shown on surgical display(s) 126 and, may further be shown on video display(s) 124 as desired. The laryngoscope image data may take up a portion of or the entire the surgical display(s) 126. Likewise, while no endoscope image data is illustrated as being shown on the surgical display(s) 126, it is understood that the laryngoscope image data may simply be overlain (e.g., in a window) on the endoscope image data, or the endoscope image data could be shut off during routing by the anesthesiologist. Any configuration that allows the anesthesiologist to immediately view the video laryngoscope data is possible.

Still another embodiment in FIG. 4 shows the laryngoscope image data presented on the touchscreen 150, which is positioned adjacent to the anesthesiologist. This could be particularly desirable as the touchscreen can be mounted on a boom or arm and be fully adjustable allowing the anesthesiologist to quickly and easily adjust the touchscreen for intubation.

Once the anesthesiologist has completed the intubation procedure, touching the input device (emergency intubate icon) 108 a second time can work to interrupt the routing of laryngoscope image data to the display(s) and reestablish the routing of endoscope image data to the display(s). It should also be noted that the routing of endoscope image data to selected storage devices may also be reestablished as well as the settings of various medical devices and equipment. For example, it may be advantageous to automatically adjust the settings of select medical tools and equipment to a predetermined setting (e.g., to a low setting or even off) in the event the input device 108 is activated.

This allows for a single button/icon to be touched to route the laryngoscope image data to selected display(s) and for a single button/icon to be touched a second time to reestablish all of the image routing and tool/equipment settings automatically without any need to reprogram the system.

Figure 5:
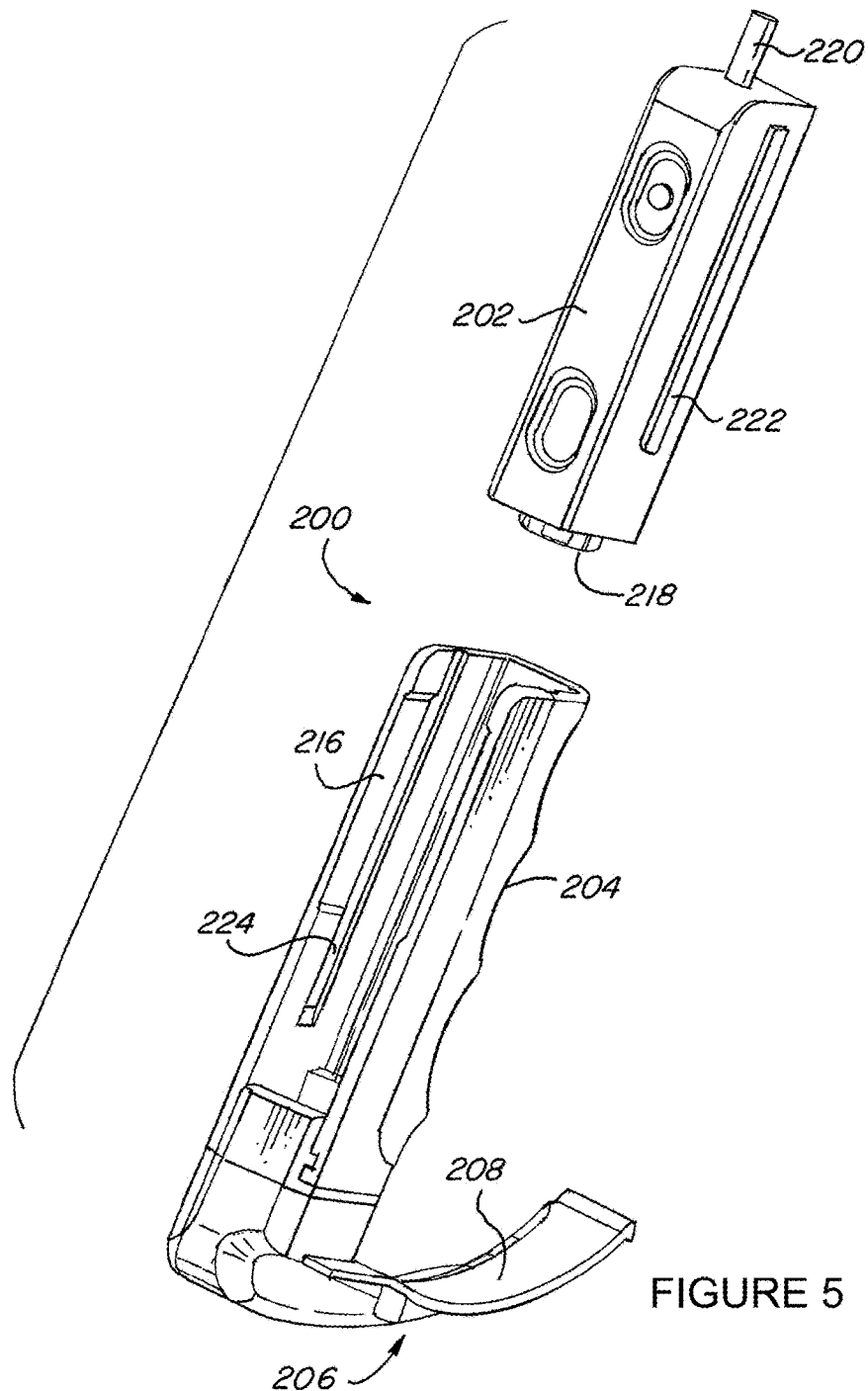
FIG. 5 is an illustration of a video laryngoscope according to an embodiment of the present invention of FIG. 1.
Figure 6:
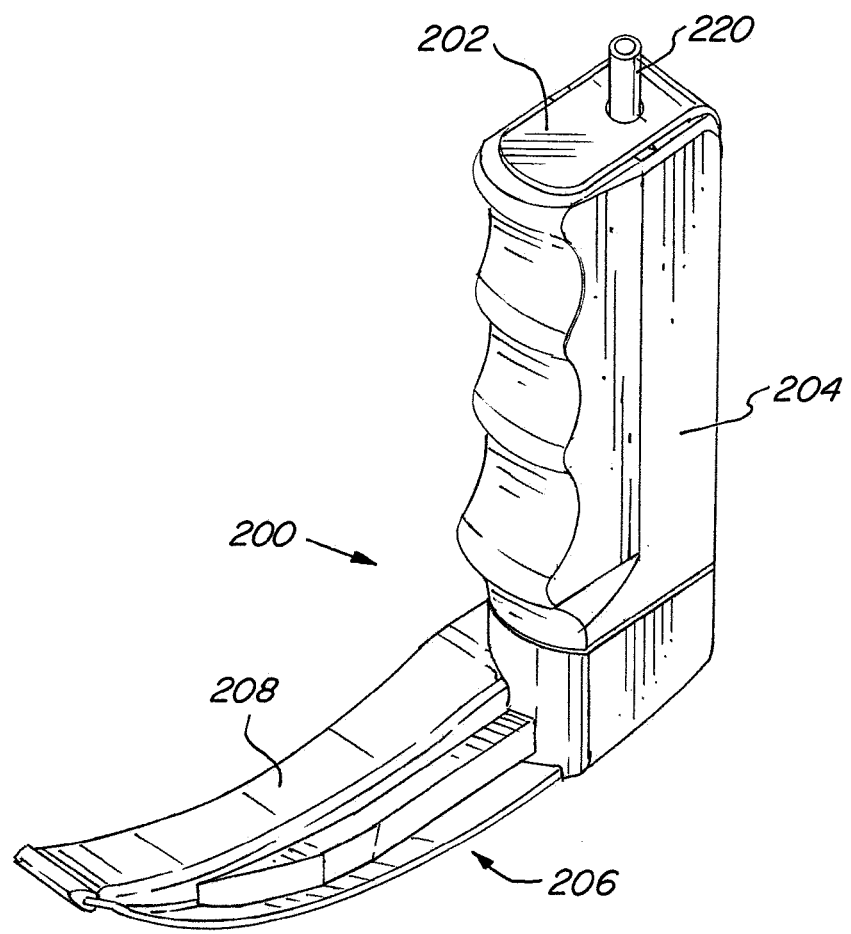
FIG. 6 is an illustration of a video laryngoscope according to an embodiment of the present invention of FIG. 1.
Figure 7:
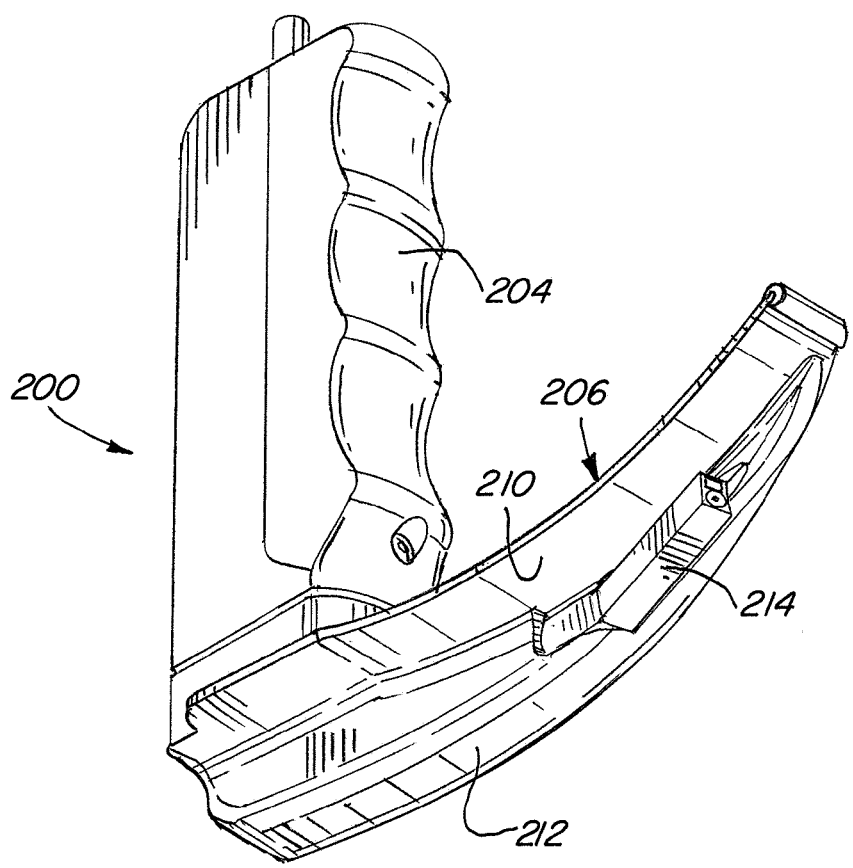
FIG. 7 is an illustration of a video laryngoscope according to an embodiment of the present invention of FIG. 1.

FIGS. 5-7 illustrate one particular embodiment of video laryngoscope 200. For example, video laryngoscope 200 may comprise a camera 202 that may be detachably connected to a handle 204 of the video laryngoscope. The handle 204 includes a blade 206 having, in this embodiment, a curved upper surface 208 and a curved lower surface 210. Also shown in FIGS. 5-7 is a bottom surface 212 within which the image channel(s) reside transmitting laryngoscope image data to camera 202. An imager 214 is provided on the underside of the blade 206.

The handle 204 is provided with a cavity 216 within which the camera 202 may be inserted and securely held. A camera connector 218 is located on one end of camera 202 and is designed to engaged with a handle connector (not shown) positioned in the bottom of cavity 216.

The camera 202 is provided with a protrusion 222, which may be in the form of a raised ridge on the exterior surface of camera 202 that is designed to engage with a recess 224 provided on an inner surface of cavity 216. In this manner, the camera 202 may be slid into cavity 216 such that the connectors engage (there may be an audible "click" when fully inserted) and the engagement of the protrusion 222 with the recess 224 maintains the camera 202 securely in cavity 216.

A connection 220 is provided at a top end of camera 202 for the transmission of laryngoscope image data. It should be understood however, that even though a portion of a cable (connection 220) is illustrated, a wireless configuration is contemplated that could provide for wireless transmission of the laryngoscope image data to the system for display on the various selected display(s).

Although the invention has been described with reference to a particular arrangement of parts, features and the like, these are not intended to exhaust all possible arrangements or features, and indeed many other modifications and variations will be ascertainable to those of skill in the art.

What is claimed is:

1. An operating room control system comprising:
   a computer having a network connection;
   a storage device accessible by said computer;
   an interface coupled to said computer;
   a first device coupled to said interface and generating endoscope image data;
   a second device coupled to said interface and generating second data;
   an input device coupled to said interface; and
   a video laryngoscope coupled to said interface and generating laryngoscope image data;
   a first display coupled to said interface wherein endoscope image data is routed to and shown on said first display when said input device is manually activated a first time by selecting said first device as an input and selecting said first display as an output to receive the endoscope image data;
   a second display coupled to said interface, wherein second data is routed to and shown on said second display when said second device is connected to the system and when said input device is manually activated a second time by selecting said second device as an input and selecting said second display as an output to receive the second data;
   wherein upon manual activation of the input device a third time by selecting said video laryngoscope as an input, routing of the endoscope image data to the first display and routing of the second data to said second display is automatically interrupted is automatically interrupted, and said first display and said second display are automatically selected by said system as the outputs such that the laryngoscope image data is automatically routed to said first display and second display; and
   wherein the operating room control system further comprises at least one medical tool and one piece of medical equipment coupled to said interface, wherein upon activation of the input device, the functioning of said at least one medical tool and one piece of medical equipment are automatically changed to a predetermined setting.

2. The operating room control system according to claim 1 wherein the predetermined setting is off.

3. The operating room control system according to claim 1 wherein routing of endoscope image data to said first display further includes routing of endoscope image data to said storage device, and upon reestablishment of the routing of endoscope image data to said first display, routing of endoscope image data to said storage device is also reestablished.

4. The operating room control system according to claim 1 wherein said input device comprises an icon on a touchscreen, and wherein upon activation of said input device, the laryngoscope image data is automatically displayed on the touchscreen.

5. The operating room control system according to claim 4 wherein medical information relating to a patient is displayed on the touchscreen.

* * * * *